United States Patent [19]

Takemura et al.

[11] Patent Number: 4,876,126
[45] Date of Patent: Oct. 24, 1989

[54] MEDICAL INSTRUMENT AND METHOD FOR MAKING

[75] Inventors: Naoto Takemura; Susumu Tanabe, both of Fujinomiya, Japan

[73] Assignee: Terumo Kabushiki Kaisha, Tokyo, Japan

[21] Appl. No.: 240,365

[22] Filed: Sep. 1, 1988

Related U.S. Application Data

[63] Continuation of Ser. No. 11,441, Feb. 5, 1987, abandoned, which is a continuation of Ser. No. 741,226, Jun. 4, 1985, abandoned.

[30] Foreign Application Priority Data

Jun. 4, 1984 [JP] Japan ................................ 59-114267
Aug. 7, 1984 [JP] Japan ................................ 59-165455

[51] Int. Cl.$^4$ .......................... A61F 5/42; A61M 25/00
[52] U.S. Cl. ................................ 428/35.7; 428/413; 428/424.2; 428/474.4; 428/507; 428/36.6; 428/36.91; 604/266; 427/2
[58] Field of Search ................ 427/2; 428/411.1, 413, 428/424.2, 425.1, 474.4, 474.7, 475.8, 476.1, 35, 36, 507; 604/266

[56] References Cited

U.S. PATENT DOCUMENTS

| | | | |
|---|---|---|---|
| 2,096,296 | 10/1937 | Fromm | 427/2 |
| 3,023,126 | 2/1962 | Underwood . | |
| 3,663,288 | 5/1972 | Miller | 604/266 |
| 3,886,947 | 6/1975 | Sawyer | 604/266 |
| 4,080,706 | 3/1978 | Heilman et al. | 427/2 X |
| 4,100,309 | 7/1978 | Micklus et al. . | |
| 4,119,094 | 10/1978 | Micklus et al. . | |
| 4,373,009 | 2/1983 | Winn . | |
| 4,459,317 | 7/1984 | Lambert | 427/2 |
| 4,459,318 | 7/1984 | Hyans | 604/266 X |
| 4,536,179 | 8/1985 | Anderson et al. | 427/2 X |

FOREIGN PATENT DOCUMENTS

| | | |
|---|---|---|
| 556350 | 10/1983 | Australia . |
| 556351 | 10/1983 | Australia . |
| 0014238 | 8/1980 | Fed. Rep. of Germany . |
| 0093094 | 11/1983 | Fed. Rep. of Germany . |
| 2321086 | 11/1984 | Fed. Rep. of Germany . |
| 53-106778 | 9/1978 | Japan . |
| 0039983 | 3/1979 | Japan ................................ 604/266 |
| 2128500 | 5/1984 | United Kingdom . |

OTHER PUBLICATIONS

Encyclopedia of Polymer Science & Technology-vol. 10, pp. 616-622.
Encyclopedia of Polymer Science & Technology-vol. 1, pp. 734-746.

Primary Examiner—Nancy A. B. Swisher
Attorney, Agent, or Firm—Cushman, Darby & Cushman

[57] ABSTRACT

A medical instrument comprises a substrate which has at least on its surface a reactive functional group covalently bonded with a water-soluble polymer or derivative thereof, whereby said surface has lubricity when wetted. The water-soluble polymer is a cellulosic polymer, maleic anhydride polymer, polyacrylamide or water-soluble nylon.

The medical instrument is prepared by treating a substrate with a solution of a compound having a reactive functional group to form an undercoat so that the reactive functional group is present at least on the substrate surface, and then treating the substrate with a water-soluble polymer or derivative thereof to covalently bond the reactive functional group with the water-soluble polymer to thereby form a coat of the water-soluble polymer on the undercoat and optionally, contacting the treated substrate with water.

26 Claims, 3 Drawing Sheets

MEDICAL INSTRUMENT AND METHOD FOR MAKING

This is a continuation of application Ser. No. 11,441 filed Feb. 5, 1987, now abandoned, which is a continuation of application Ser. No. 741,226, filed June 4, 1985, now abandoned.

BACKGROUND OF THE INVENTION

This invention relates to a medical instrument and a method for the surface treatment thereof.

Medical appliances, for example, medical instruments such as catheters which are inserted through airway, trachea, alimentary canal, urethra, blood vessels or other celoms or tissues, and medical instruments such as guide wires or stylets which are inserted through catheters are required to have smoothness for assuring the introduction of such medical instruments into a desired region of the body without injuring tissues. Such medical instruments are further required to have lubricity for preventing injury or inflammation of mucous membrane which would be caused when the instruments stay in the tissues.

For this reason, substrates of which such medical instruments are made are, heretofore, made of ordinary low-frictional resistance materials such as fluoroplastics and polyethylene, or coated with a surface layer of fluoroplastics, silicone or the like. In another instance, silicone oil, olive oil, glycerine, xylocain jelly or the like is applied to the substrate surface.

However, these conventional techniques are not satisfactory in effect. For example, in case low-frictional resistance materials such as Teflon (trade mark, manufactured by DuPont), high-density polyethylene, etc. are employed or substrates are coated with a surface coat of such materials, there is the problem that coefficients of friction are not low enough. In case oils are applied, coefficients of dynamic friction are sufficiently low, but there is another problem that oils tends to run off and the effect does not last. In addition, products with oil applied has smeary surfaces and are difficult to store. Therefore, oil application must be done immediately before use, which would make the handling complicated.

U.S. Pat. No. 4,100,309 discloses the use of an interpolymer of polyvinyl pyrrolidone and polyurethane as a coating layer on the outer and inner surfaces of a catheter tube. This coating layer is superior in frictional resistance and its retention to other types of conventional coatings.

This coating layer, however, needs an isocyanate group as a reactive functional group and polyurethane as a substrate or an undercoat on a substrate. Thus, the choice of the substrate and the application of the resultant medical instrument are disadvantageously limited. For example, if such a coating layer is applied to a polyamide resin, it is difficult to directly introduce isocyanate group. Even if polyurethane is used as an undercoat, bonding to the substrate is not good and formation of a durable coating layer is not expected. In addition, polyvinyl pyrrolidone is relatively expensive.

Furthermore, it is considered that polyvinyl pyrrolidone and isocyanate group forms an ion complex. Therefore, the bond is not stable in aqueous solutions for example, humor such as saliva, digestive fluid, blood or the like, or physiological saline and the complex tends to be dissolved in such solution. Thus, lasting effect is not expected. The retention of low frictional resistance is very important for medical tube guides which are used under severe sliding conditions as contemplated in the present invention.

The above-mentioned U.S. Patent includes no disclosure or indication that the coating layer can be applied to catheter guides as in the present invention, thereby remarkably improving the sliding resistance thereof and solving the problems of manipulation and safety.

Japanese Patent Application Kokai No. 53-106778 discloses a method for providing a fibrinolytic activity to the surface of polyurethane resins wherein fibrinolysis activators are affixed to the surface of polyurethane resins. According to this disclosure, a polymer containing maleic anhydride units is used as an intermediate bonding layer for affixing the fibrinolysis activator on the polyurethane surface so that the layer of fibrinolysis activator formed as an outer surface may be dissolved to provide anticoagulant properties. There is no disclosure or suggestion of enhancing the lubricity of medical instruments.

Guide wires which are typical of medical instruments have the following problems.

The medical guide wires used in the prior art generally include coiled guide wires formed of stainless steel or piano wires and monofilament-like guide wires formed of plastic materials. In order that the guide wire has a flexible tip and a relatively rigid base, the guide wire is constructed so as to include a core of general metals such as stainless steel and piano wires partially or entirely in the interior thereof.

As typically encountered in indwelling a vasographic catheter at the predetermined vessel site, the guide wire is inserted through a catheter up to its tip opening, the catheter with the guide wire is inserted into the blood vessel through an introduction needle percutaneously, and the catheter was further inserted through the vessel by using the guide wire as a leading and supporting guide.

In order that the catheter tip reaches the destined vessel site, the guide wire tip protrudes a distance of a few centimeters beyond the distal opening of the catheter. The exposed or extended tip portion of the guide wire is advanced through the vessel in contact with the inner wall of the vessel. The tip portion should be sufficiently soft and flexible so that it may easily conform to irregularities on the vessel inner wall and bends at vessel branches to effectively guide the catheter.

In such operation, it is first of all desired that the frictional resistance between the catheter inner surface and the guide wire is low. Relatively high friction between the catheter and the guide wire not only prevents the guide wire from being inserted through the catheter, but the guide wire from being slidingly moved through the catheter, making it difficult to carry out subtle indwelling operation at the destined vessel site. Sometimes the guide wire cannot be withdrawn from the catheter, rendering the catheter lumen unusable despite the completion of indwelling operation.

To avoid such inconvenience, attempts have been made in the prior art to apply low frictional resistance Teflon and silicone oil to the outer surface of guide wires. Application of silicone oil fails to retain lubricity because of immediate loss of silicone coatings. Frequent applications add to frictional resistance, also undesirably creating troubles as mentioned above.

These attempts are still insufficient. There is thus the need for a guide wire having a lower frictional resistance surface which enables more subtle operation in a vessel as well as in the associated catheter and can be easily indwelled at the site where catheters are otherwise difficult to stay.

A second problem is encountered when the guide wire tip preceding the catheter is advanced through the vessel. When the guide wire tip passes a plurality of vessel branches or complicated branches or slender branches suddenly from a thick vessel, the guide wire tip is first abutted against the branch. It must be observed whether the tip is deflected to the right or the left. The guide wire is further advanced when the tip turns on the side of the destined site.

It is thus necessary that the guide wire tip can move along the vessel wall in a sliding manner with a sufficiently low force. Tip portions used in the prior art are made as flexible as possible, but still insufficient. One recent attempt is to form a spherical tip to weaken the impact of the tip against the vessel wall and to locally concentrate a force to the base of the spherical tip to provide ease of bending, thereby facilitating lateral motion of the tip. As the tip is further guided to the second and third branches, the tip experiences increased resistance to the vessel wall. Since the catheter is also advanced in curved form, the guide wire experiences increased friction within the catheter, making the inserting operation less smooth.

SUMMARY OF THE INVENTION

It is an object of the present invention to provide a medical instrument which exhibits low frictional resistance upon insertion when wetted with aqueous solution, for example, humor such as saliva, digestive fluid, blood, etc., physiological saline or water, ha excellent retention and shelf stability, and has a coating layer which allows the substrate to be made of a variety of materials.

It is another object of the present invention to provide a method for preparing such a medical instrument.

It is a further object of the present invention to provide a guide wire for use in a catheter, which presents a continuously lubricating surface having a remarkably low frictional resistance when wetted with aqueous fluid, for example, humor such as saliva, digestive fluid and blood, physiological saline, and water, thereby ensuring ease of operation of the guide wire through the catheter.

These objects can be attained by the present invention as defined below.

According to a first aspect of the present invention, there is provided a medical instrument comprising a substrate having a surface. The substrate has at least on its surface a reactive functional group which is covalently bonded with a water-soluble polymer or derivative thereof. The water-soluble polymer is a cellulosic polymer, a maleic anhydride polymer, a polyacrylamide, or a water-soluble nylon. The surface thus exhibits lubricity when wetted.

According to a second aspect of the present invention, there is provided a method for preparing a medical instrument, comprising treating a substrate constituting the medical instrument and having a surface with a solution of a compound having a reactive functional group to form an undercoat so that the reactive functional group is present at least on the surface of the substrate, and then treating the substrate with a water-soluble polymer or derivative thereof to covalently bond the reactive functional group with the water-soluble polymer to thereby form a coat of the water-soluble polymer on the undercoat and thereafter optionally contacting the treated substrate with water so that the surface may have lubricity when wetted.

The water-soluble polymer is a cellulosic polymer, a maleic anhydride polymer, a polyacrylamide, or a water-soluble nylon. More preferably the cellulosic polymer is hydroxypropyl cellulose, and the maleic anhydride polymer is a copolymer of methyl vinyl ether and maleic anhydride. It is also preferred that the reactive functional group be an aldehyde group, an epoxy group, an isocyanate group or an amino group. The medical instrument is a guide member formed of wire member insertable through a medical tubing for allowing the medical tubing to be moved and out of a body.

DETAILED DESCRIPTION OF THE INVENTION

The present invention will be described in detail.

One class of the water-soluble polymers employed to form a lubricating surface coating layer on a medical instrument such as a medical tube guide includes polymers which are attached to a substrate of the medical instrument through covalent bond. The water-soluble polymers are generally chain-structured, non-crosslinked polymers having a hydrophilic group such as —OH, —CONH$_2$, —COOH, —NH$_2$, —COO$^-$, —SO$_3^-$, and —NR$_3^+$ where R is alkyl or hydrogen. Examples are mentioned below. Natural water-soluble polymers (1) Starches
   carboxymethyl starch, dialdehyde starch
(2) Celluloses
   CMC, MC, HEC, HPC
(3) Tannins and lignins
   tannin, lignin
(4) Polysaccharides
   alginic acid, gum arabic, gum guar, gum tragacanth, tamarind
(5) Proteins
   gelatin, casein, glue, collagen Synthetic water-soluble polymers
(1) PVA
   polyvinyl alcohol
(2) Polyethylene oxides
   polyethylene oxide, polyethylene glycol
(3) Acrylates
   sodium polyacrylate
(4) Maleic anhydride polymers
   methyl vinyl ether-maleic anhydride copolymers
(5) Phthalates
   polyhydroxy ethyl phthalates
(6) Water-soluble polyesters
   polydimethylol propionate
(7) Ketone aldehyde resins
   methyl isopropyl ketone formaldehyde resin
(8) Acrylamides polyacrylamide
(9) Polyvinyl pyrrolidone
   PVP
(10) Polyamines
   polyethylene imine
(11) Poly-electrolytes
   polystyrene sulfonate
(12) Others
   Water-soluble nylon The derivatives of these polymers are not limited to water-soluble ones but may be of any form so long as they have, as a basic structure, the water-soluble polymer as mentioned above. Insolubilized derivatives may also be employed so long as they have freedom in molecular chain and can be hydrated as will be discussed hereinafter.

Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation or reduction reaction of the above-mentioned water-soluble polymers. Also included are polymers crosslinked with substances having more than one reactive functional group such as diazonium group, azide group, isocyanate group, acid chloride group, acid anhydride group, imino carbonate group, amino group, carboxyl group, epoxy group, hydroxyl group, and aldehyde group. Also included are copolymers with vinyl compounds, acrylic acid, methacrylic acid, diene compounds, and maleic anhydride.

The water-soluble polymers are easily soluble in water. If the solution is present between articles, it can remarkably lower the frictional resistance therebetween and thus serves as a lubricant. The derivatives of the water-soluble polymers which are obtained by condensation, addition or replacement reaction, and partially crosslinked or insolubilized polymers are also effective as lubricants between two layers.

When these polymers are covalently bonded with a reactive functional group existing on or introduced in the surface of a substrate, a lubricating layer carried on the substrate can be obtained. The lubricating layer is not soluble in water and offer a lasting lubricating surface. The type of water-soluble polymer is not critical, but there can be mentioned, as typical examples, celluloses, maleic anhydride polymers, acrylamides, water-soluble nylons or the like. Among these, hydroxypropyl cellulose, methyl vinyl ether-maleic anhydride copolymer, polyacrylamide, and water-soluble nylon (AQ-nylon P-70 manufactured and sold by Toray Industries, Inc.) are easily available at a reasonable cost and excellent in safety.

The average molecular weight of these water-soluble high polymers is not critical. Polymers having an average molecular weight of 30,000 to 5,000,000 are preferable because they are excellent in lubricity and can yield a lubricant layer of appropriate thickness and not too swellable when it is hydrated.

Other examples of the water-soluble polymers which are used to form a lubricating coating layer on medical instruments such as medical tube guides according to the present invention are those attached to the substrate of the medical instrument through ionic bonds.

Typical examples of the water-soluble polymers include, in addition to polyvinyl pyrrolidone, carboxylates, sulfonates, and ammonium salts of the above-listed water-soluble polymers. More illustratively, examples of the carboxylates include a sodium salt of methyl vinyl ether-maleic anhydride, sodium polyacrylate, polyacrylamide hydrolyzate, sodium carboxymethyl cellulose, and sodium alginate; examples of the sulfonates include sodium polystyrenesulfonate and sodium polyvinylsulfonate; and examples of the ammonium salts include ammonium salts of methyl vinyl ether-maleic anhydride and quaternized polyacrylamide.

The control of swelling upon hydration may be effected by using insolubilized materials as described above or by performing a similar treatment after water-soluble polymers are applied to substrates.

The reactive functional groups existing on or introduced in the substrate surface are not particularly limited as long as they are reactive, bondable and crosslinkable with the water-soluble high polymers to affix the same. Examples of the reactive functional groups include a diazonium group, azide group, isocyanate group, acid chloride group, acid anhydride group, iminocarbonate group, amino group, carboxyl group, epoxy group, hydroxyl group, and aldehyde group. Among these, isocyanate, amino, aldehyde, and epoxy groups are preferred.

Therefore, polyurethanes, polyamides and the like are preferred as the reactive functional group containing substrates. In general, substrates commonly used to constitute outer or inner walls of various medical instruments such as medical tube guides do not contain such a reactive functional group. In these cases, the substrates are pre-treated with substances having a reactive functional group so that the reactive functional group may be present in or on the substrates, and the water-soluble polymer as specified by the present invention is covalently bonded therewith. The form of bond may include covalent bond, ionic bond, physical adsorption, etc. The covalent bond is most preferred in retention, although the ionic bond is allowable.

Such treatment is not always required to be applied directly on the surface of the substrate, but the reactive functional group may exist on or be introduced in the polymer layer so as to be covalently bonded with the water-soluble high polymer as described above to obtain a continuously lubricating surface.

Examples of the substances having the reactive functional group include polyisocyanates such as ethylene diisocyanate, hexamethylene diisocyanate, xylene diisocyanate, toluene diisocyanate, diphenyl methane diisocyanate, naphthalene diisocyanate, phenylene diisocyanate, cyclohexylene diisocyanate, triphenylmethane triisocyanate, toluene triisocyanate, or the like; and adducts and prepolymers of these polyisocyanates with polyols.

Examples of low molecular weight polyamines include ethylenediamine, trimethylendiamine, 1,2-diaminopropane, tetramethylenediamine, 1,3-diaminobutane, 2,3-diaminobutane, pentamethylenediamine, 2,4-diaminopentane, hexamethylenediamine, octamethylenediamine, nonamethylenediamine, decamethylenediamine, undecamethylenediamine, dodecamethylenediamine, tridecamethylenediamine, octadecamethylenediamine, N,N-dimethyl ethylenediamine, N,N-diethyl trimethylenediamine, N,N-dimethyl trimethylenediamine, N,N-dibutyl trimethylenediamine, N,N,N'-triethyl ethylenediamine, N-methyl trimethylenediamine, N,N-dimethyl-p-phenylenediamine, N,N-dimethyl hexamethylenediamine, diethylenetriamine, triethylene tetramine, tetraethylene pentamine, heptaethylene octamine, nonaethylene decamine, 1,3- bis(2'-aminoethylamino)propane, bis(3-aminopropal)amine, 1,3-bis(3'-aminopropylamino)propane, 1,2,3-triaminopropane, tris(2-aminoethyl)amine, tetra(aminomethyl)methane, methyl iminobispropylamine, methyliminobisethylamine, ethyliminobisethylamine, N-aminopropyl-2-morpholine, N-aminopropyl-2-pipecoline, N-(2-hydroxyethyl)trimethylenediamine, xylenediamine, phenylenediamine, piperazine, N-methylpiperazine, N-(2-aminoethyl)ethanolamine, N-aminoethylpiperazine, N,N,N',N'-tetramethyl ethylenediamine, N,N,N',N'-tetramethyl tetramethylenediamine, or the like. Examples of high molecular weight polyamines include (I) poly(alkylene polyamines) synthesized from amines and alkylene dihalides or epichlorohydrin (see Encyclopedia of Polymer Science and Technology, Vol. 10., p. 616); (II) alkylene imine polymers obtained by ring opening-polymerization of alkylene imines such as ethylene imine, propylene imine, etc. (see Encyclopedia of Polymer Science and Technology, Vol. 1, p. 734); and (III) other polyamines such as polyvinyl amine, polylysine.

Also included are polyaldehydes such as glutaraldehyde, tereohthalaldehyde, isophthalaldehyde, dialdehyde, starch, glyoxal, malonaldehyde, succinaldehyde, adipaldehyde, pimelinaldehyde, suberinaldehyde, maleinaldehyde, 2-pentene-1,5-dialdehyde, and the like.

Also included are polyepoxides such as ethylene glycol diglycidyl ether, polyethylene glycol diglycidyl ether, propylene glycol diglycidyl ether, polypropylene diglycidyl ether, hexanediol diglycidyl ether, trimethylolpropane triglycidyl ether, and the like.

Among these, adducts of 4,4'-diphenylmethane diisocyanate and tolylenediisocyante with trimethylolpropane, an adduct of hexamethylene diisocyanate with trimethylolpropane, or trimers thereof and diethylenetriamine are most preferable.

In the present invention, even if the outer layer of the substrate is not of a low frictional resistance material or the substrate is not coated prior to use with a low frictional resistance imparting agent such as silicone oil, olive oil, glycerine, xylocain jelly, a low frictional resistant or lubricating surface condition is obtained upon contact with aqueous solutions as described above, which is suitable as medical instruments like tube guides.

Substantially little limit is imposed on the material of the substrate to be used. The substrates may, for example, be various types of organic high polymer substrates such as polyamide, polyester, polyvinyl chloride, polystyrene, polyacrylate, polymetacrylate, polyacrylonitrile, polyacrylamide, polyacrylic acid, polymethacrylic acid, polyethylene, polypropylene, polyvinyl alcohol, polymaleic anhydride, polyethylene imine, polyurethane, polyvinyl acetate, silicone resins, latexes, and copolymers and blends thereof; and various types of inorganic and metal substances such as glass, ceramic, stainless steel and the like. These substrates may optionally contain various additives.

Among these, organic polymer resins have good lubricity retention and especially, polyvinyl chlorides, polyurethanes, polyamides, latexes, and polyesters are most effective.

In case resins other than the organic polymer resins as specified above, or metals or glasses are used as the substrates, desired results are obtained by preforming a layer of said organic polymer resins on the substrate surface to introduce the reactive functional group or by blending the other resins with the reactive functional group-containing substance to form lubricating layers.

The formation of the coat layer on the substrate according to the present invention may be made as follows:

Where an ordinary substrate which does not contain the reactive functional group is used, an undercoat is first formed. The undercoat may be formed by dipping the substrate in a solution containing the compound having the reactive functional group as specified above followed by drying.

In this case, the solvent employed may be selected from, for example, ketones such as methyl ethyl ketone, methyl isobutyl ketone, cyclohexanone, etc.; esters such as ethyl acetate, butyl acetate, carbitol acetate, butyl carbitol acetate, etc.; ethers such as methyl cellosolve, ethyl cellosolve, tetrahydrofuran, etc.; aromatics such as toluene, xylene, etc.; halogenated alkyls such as dichloroethane, etc.; and alcohols.

The solvent may preferably dissolve or swell the resin substrate or the resin coating layer preformed on the substrate surface as the case may be. This leads to increased bond strength of the coating layer and enhanced retention. In this respect, methyl ethyl ketone, cyclohexanone, tetrahydrofuran, xylene, methyl alcohol are especially suitable.

The treatment may be effected by brushing or spin coating as well as dipping. The succeeding drying step is for evaporating the solvent used and may generally be carried out at a temperature of room temperature to about 80° C. for about 5 minutes to about 48 hours.

When an adhesive layer is previously formed on the substrate surface as referred to above, a conventional method may be employed.

Thereafter, the substrate with or without the undercoat formed is treated with a solution containing the water-soluble polymer as specified in the present invention.

The solvent used for the solution may be selected from solvents which are not reactive with the reactive functional group in the substrate or the undercoat layer, i.e., not reactive with isocyanate group or amino group. Especially, methyl ethyl ketone, THF, acetone and the like are suitable. In particular, the solvents which can dissolve or swell the substrate are preferred. The concentration of the solution is preferably 0.1 to 15%, and more particularly 0.5 to 10%.

The treatment is ordinarily effected by dipping as in the case of the undercoat treatment described above, but other coating methods may also be employed. The treating temperature is room temperature to about 80° C. and the treating time is about 1 second to about 48 hours. The subsequent drying is effected at a temperature of room temperature to about 80° C. for about 5 minutes to about 48 hours.

In this way, the water-soluble polymer is convalently bonded with the reactive functional group to form a coating layer according to the present invention.

According to the present invention, the thus formed coating layer may preferably be further contacted with water. This water treatment provides such a desirable result that affinity to water can be obtained within a short time.

The water treatment is ordinarily carried out by dipping the substrate with the coating layer in water followed by drying. The dipping time is about 10 minutes to about 2 hours and the treating temperature is room temperature to about 60° C., and the drying is carried out at a temperature of room temperature to about 80° C. for about 30 minutes to about 48 hours.

The water treatment may also be carried out with steam.

The mechanism the coating layer of the water-soluble polymer affixed through covalent bond to the substrate in the present invention retains excellent lubricity for a long time is not apparent, but it may be explained as follows. It is to be noted that the water soluble polymers of ionic bond type provide a lower bonding force and hence shorter lubricity retention than those of covalent bond type.

The water-soluble polymer is hydrated through a hydrophilic group such as $-NH_2$, $-COOH$, and $-OH$ when it is in the form of an aqueous solution or gel. Although the hydrated state is not clearly known, it is considered that there are bonding water which is incorporated in the polymer and can hardly move and free water having a high degree of freedom.

The development of lubricity by the treated substrate when wetted with water is presumed to be due to such free water. It is due to the lack of free water that some polymers can well absorb water to swell but lack lubricity and relatively low molecular weight polymers exhibit low lubricity. The lubricity development is thus considered to be influenced by the structure and polarity of polymers.

More particularly, substances such as cellulosic polymers whose molecular structure is enough crystalline have less free water and the movement of their molecule is not smooth as compared with polymers of chain structure. For this reason, CMC and HPC are rather poor in lubricity, while PVM/MA (e.g., GANTREZ), PVP, PAAm, etc. have excellent lubricity.

However, if a polymer having a chain structure and hydrophilic group is bonded to the substrate at many sites or if its molecules are crosslinked with each other, the molecules themselves lose freedom and lubricity is lowered.

A strong bond with the substrate as achieved by covalent bond is advantageous for the retention of lubricity. Therefore, where the water-soluble high polymer is affixed to the substrate through covalent bond and the chain structure molecule having a hydrophilic group extends long, there is obtained the best lubricity.

In the present invention, the medical instrument having an inner or outer surface presented by the thus treated substrate provides the surface with a required low frictional resistance when wetted with aqueous fluid as described above at the time of inserting or dwelling in a body.

The medical instrument of the present invention may be applied to the following tools by providing on the surface thereof the coating layer of the present invention.

(1) The outer or inner surface of catheters such as stomach tube catheters, nutrient catheters and ED (per tube nutrition) tubes, which are inserted into or allowed to dwell in digestive tube perorally or pernasorly.

Figure 1:
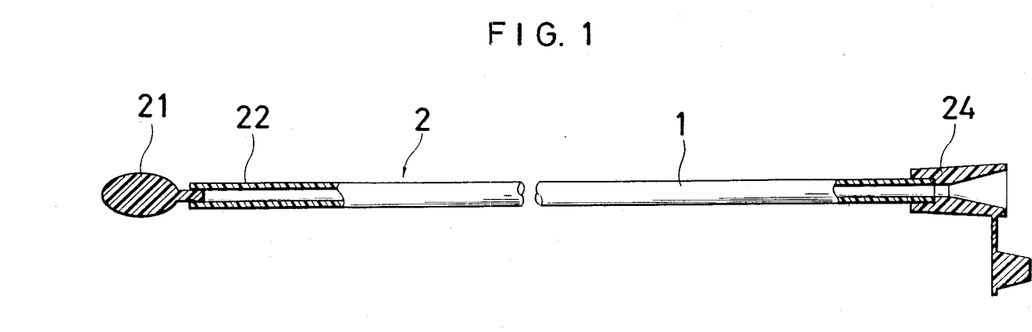
FIGS. 1, 2, 3 and 4 show medical instruments according to different embodiments of the present invention, FIG. 1, 2, 3 and 4 being side elevational views of an ED tube, a balloon catheter, a coronary vasographic catheter, and a guide wire, respectively.

For example, FIG. 1 illustrates an embodiment wherein a coating layer 1 of the present invention is formed on the outer surfaces of an olive 21 and a body tube 22 of an ED tube 2 which is coupled to a connector 24. With this coating, the tube can be easily inserted and deglutition by the patient becomes easier, too.

(2) The outer or inner surface of a tube or cuff of a catheter such as an oxygen catheter, oxygen canula or endotracheal tube, a tube or cuff of a tracheotomy tube, and an endotracheal aspiration catheter, which are inserted into or allowed to dwell in an airway or trachea through mouth or nose.

(3) The outer or inner surface of a catheter or balloon of an urethral catheter, urine introducing catheter and balloon catheter which are inserted into or allowed to dwell in an urethra.

Figure 2:
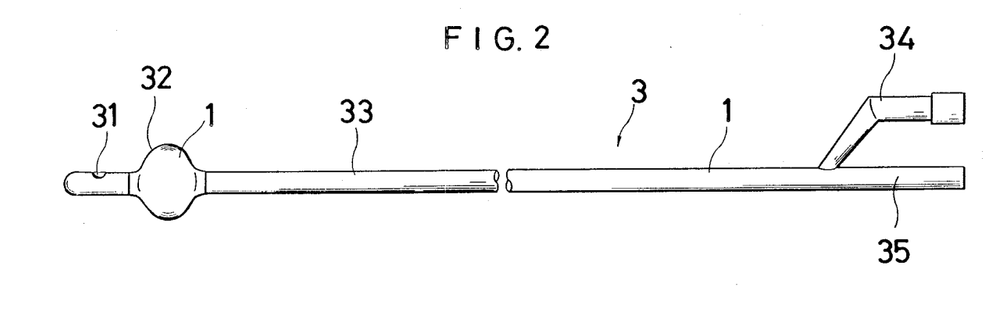

For example, FIG. 2 illustrates an embodiment wherein a coating layer 1 of the present invention is formed on the outer surface of a balloon 32 and a body tube 33 of a balloon catheter 3 which comprises a side opening 31, the balloon 32, the body tube 33, a branched pipe 34 and a body connector 35.

In this embodiment, the frictional resistance is low so that the insertion becomes easier and the pain of the patient is reduced. In addition, since the frictional resistance against mucous membranes is low, there is little fear of inflammation or injury which would be caused when the catheter stays in the tissue. It is to be noted that the coating layer of the present invention may be applied to a resilient member like the balloon 32 without changing the physical properties thereof. Since the balloon would otherwise have very high resistance upon insertion, the lubricating effect of the coating layer on the balloon is great.

(4) The outer or inner surface of catheters such as a suction catheter, drainage catheter and intestinum rectum catheter, which are inserted or allowed to dwell in various body cavities or tissues.

When the coating layer of the present invention is also formed on the inner surface of the catheters as mentioned in (1) to (4) supra, deposition of nutrients or humor to the inner wall of the catheters is reduced so as to avoid blocking of the lumen passages.

(5) The outer or inner surface of catheters such as an indwelling needle, IVH catheter, thermodilution catheter, vasographic catheter, dilator and introducer, which are inserted or allowed to dwell in a blood vessel.

If wet surface lubricity is imparted to a variety of medical tube guides as used in such catheters according to the present invention, the sliding resistance through the catheter is remarkably reduced to provide improved operability, allowing the catheter to be adequately guided to the destined site with little influence on the contacting tissues. In addition, the guide may be smoothly withdrawn from the catheter.

Figure 3:
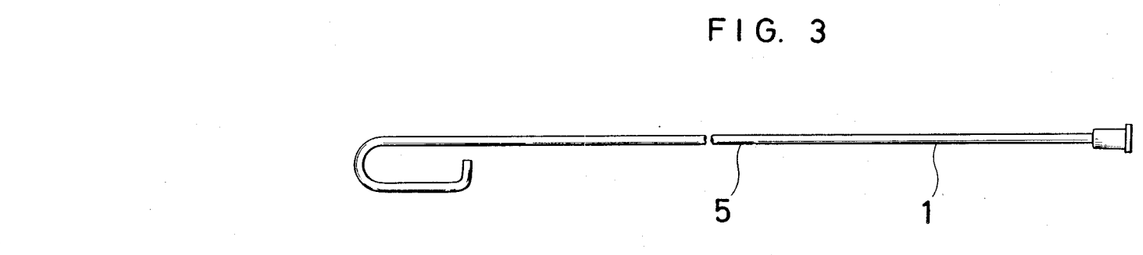
Figure 4:
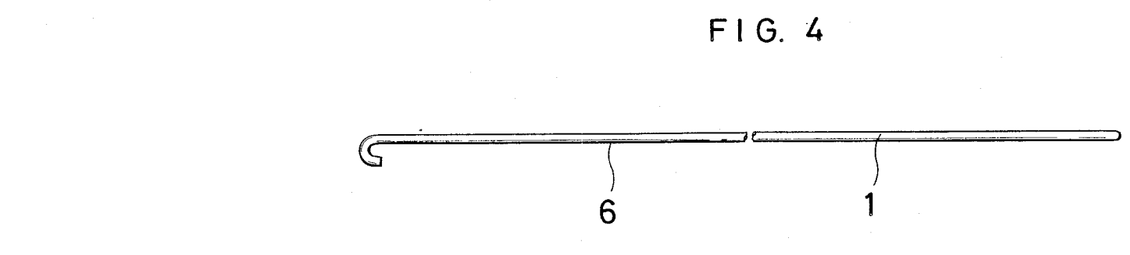

For example, FIG. 3 illustrates an embodiment wherein a coating layer 1 of the present invention is formed on the outer and inner surfaces of a coronary vasographic catheter of Judkins type. FIG. 4 illustrates an embodiment wherein a coating layer 1 of the present invention is formed on the outer surface of a guide wire 6 which is inserted through the catheter 5 so as to enable the catheter to be introduced into a blood vessel region.

For example, when the tube guide or guide wire 6 shown in FIG. 4 is combined with the coronary vasographic catheter 5 of Judkins type shown in FIG. 3, the guide wire 6 is inserted through the catheter 5 for assisting in introducing the catheter 5 into a blood vessel to the destined site.

The guide wire having the coating layer according to the present invention offers a surface having a very low frictional resistance when wetted with aqueous fluids, for example, blood and physiological saline, or oil solubility so that the sliding resistance of the wire through the catheter is very low, facilitating the operation of the guide wire through the catheter. The catheter with the guide wire of the present invention can be smoothly inserted into a vessel branch because the low frictional resistance of the guide wire to the vessel wall allows the guide wire tip in abutment with the vessel wall or vessel branch to change its direction. When the catheter is introduced into a vessel of more complicated configuration or to the second or third branch, the catheter guide wire can be readily inserted in advance without increasing the frictional resistance. The guide wire can maintain its wet lubricity without regard to frequent repeated operations of bending and advance.

(6) The outer surface of an endoscope to be inserted into various body cavities.

(7) The surface of condoms, contact lens, etc.

EFFECTS OF THE INVENTION

According to the first aspect of the invention, the frictional resistance of the surface of the medical instrument is remarkably reduced. Especially, in a wet condition, i.e., when wetted with aqueous fluid, for example humor such as saliva, digestive fluid, blood, or physiological saline or water, the frictional resistance is extremely low. The medical instrument has great advantages including ease of insertion, reduction of patient's pain, avoidance of injury of mucous membranes or inner walls of blood vessels.

Furthermore, since the coating layer can accommodate with various types of reactive functional groups, there is little limit in the materials employable for the substrate. Therefore, the coating layer of the present invention can be applied to various medical instruments, increasing the application use.

Besides, the coating layer can be offered at a cost lower than conventional ones.

According to the second aspect of the invention, a coating layer which develops lubricity, i.e. low frictional resistance in a wet condition can be obtained. If water treatment is further effected, water is incorporated in a hydrophilic group of the water-soluble polymer in the coating layer as hydrated or bound water, and a hydrous coating layer of oriented polymers having one end affixed to the substrate through covalent bond is obtained.

Although the coating layer is once dried, it can develop lubricity in a short time because of its increased affinity to water when it is brought into contact with aqueous fluid.

The as-applied coating layer is somewhat slower in development of lubricity as compared with the water-treated coating layer. It has been found that the former can have lubricity equal to the latter after the lapse of time. Thus, the coating layer according to the second aspect of the invention may be suitably used for the instrument which does not require quick development of lubricity.

Examples of the present invention are presented below by way of illustration and not by way of limitation. Many examples use sheet-like substrates rather than elongated slender guide members because sheet-like specimens are convenient to examine for lubricity and its retention. Of course, equivalent effects are obtained when these substrates are formed into any desired guide member shape.

EXAMPLE 1

A 3 cm×5 cm×0.4 mm (thick) piece of flexible polyvinyl chloride was dipped in a 1% solution of 4,4'-diphenylmethane diisocyanate in MEK for 1 minute and dried at a temperature of 60° C. for 30 minutes. The piece was then dipped in a 1.25% solution of a methyl vinyl ether-maleic anhydride copolymer (GANTREZ AN-139, MW=750,000, manufactured by G.A.F. Corporation in MEK for 10 seconds and dried at a temperature of 60° C. for 2 hours to obtain a surface lubricity imparted specimen (1).

Specimen (1) was subjected to frictional resistance and retention tests as will be described later. It was found that a frictional resistance u of 0.02 was retained even after a continuous water washing for 6 hours. The surface had not low frictional resistance immediately after the specimen was wetted with water. The desired condition was reached after the lapse of some time.

Specimen (1) after its preparation was dipped in water at room temperature for 30 minutes and dried at a temperature of 60° C. for 24 hours to obtain a specimen (2). Specimen (2) was also subjected to the same tests as done for specimen (1). It was found that the frictional resistance $\mu$ of 0.02 was maintained after a continuous water washing for 6 hours. Specimen (2) developed surface lubricity relatively rapidly after it had been wetted with water as opposed to specimen (1).

Specimen (1) after its preparation was dipped in water at room temperature for more than 1 hour and dried at 60° C. for 24 hours to obtain a specimen (3). Specimen (3) was also subjected to the same test as done for specimens (1) and (2) to find that the frictional resistance $\mu$ of 0.02 was kept after a continuous water washing for 6 hours. Specimen (3) developed surface lubricity immediately after it had been wetted with water, which was superior to specimens (1) and (2).

EXAMPLE 2

A 3 cm×5 cm×0.4 mm (thick) piece of flexible polyvinyl chloride was dipped in an aqueous solution of 5 wt % diethylene triamine and 5 wt % tetra-n-butyl ammonium iodide at a temperature of 60° C. for 10 minutes and dried at 60° C. for 30 minutes. It was then dipped in a 2.5% MEK solution of a methyl vinyl ether-maleic anhydride copolymer (GANTREZ AN-139) for 10 seconds and dried at 60° C. for 2 hours. It was further dipped in water for 1 hour for water contact and dried at 60° C. for 24 hours to obtain a surface lubricity imparted specimen (4).

EXAMPLE 3

A polyurethane resin terminated with an isocyanate group was synthesized by reacting 10 g of polyethyleneglycol (MW=1,000), 4 g of pentaerythritol and 16 g of toluene diisocyanate. The polyurethane resin was molded into a sheet of 3 cm×5 cm×0.4 mm (thick). The sheet was dipped in a 1.25% MEK solution of a methyl vinyl ether-maleic anhydride copolymer for 10 seconds, dried at 60° C. for 2 hours, dipped in water at room temperature for more than 1 hour, and dried at 60° C. for 24 hours to obtain a surface lubricity treated specimen (5).

In the frictional resistance test and the retention test, this specimen showed excellent performance as in the case of specimen (3).

EXAMPLE 4

A 3 cm×5 cm×0.4 mm (thick) piece of 6-nylon was dipped in dilute hydrochloric acid at 30° C. for 60 minutes, sufficiently rinsed with water, dipped in a 1:2 mixture of a 10% aqueous solution of polyethylene imine and a 5% methanol solution of dicyclohexyl carbodiimide at a temperature of 30° C. for 5 hours, and rinsed with water. It was then dipped in a 1.25 MEK solution of a methyl vinyl ether-maleic anhydride copolymer for 10 minutes and dried at a temperature of 60° C. for 2 hours. It was further dipped in water at room temperature for more than 1 hour for water contact and dried at 60° C. for 24 hours to obtain a surface lubricity treated specimen (6).

This specimen showed excellent lubricity and retention in the frictional resistance and retention tests.

EXAMPLE 5

A stainless steel wire having a diameter of 0.87 mm and a length of 100 cm was dipped in a 1:1 mixture of a 5% THF solution of polyurethane and a 2% MEK solution of 4,4'-diphenylmethane diisocyanate and dried at 60° C. for 1 hour. It was then dipped in a 2.5% MEK solution of methyl vinyl ether-maleic anhydride copolymer (GANTREZ AN-169, MW=1,500,000, manufactured by G.A.F. Corporation) for 1 minute and dried at 60° C. for 30 minutes. It was further dipped in water for 3 hours for water contact and dried at 60° C. for 24 hours to obtain a surface lubricity imparted catheter guide wire (7).

Guide wire (7) was wetted with physiological saline before it was inserted and operated through a 7Fr vasographic catheter. The performance was satisfactory with a very low sliding resistance.

EXAMPLE 6

A 3 cm×5 cm×0.4 mm (thick) piece of 6-nylon was dipped in a 1% MEK solution of 4,4'-diphenylmethane diisocyanate for 1 hour and dried at 60° C. for 30 minutes. It was then dipped in a 1% MEK solution of methyl vinyl ether-maleic anhydride copolymer (GANTREZ AN-169, MW=1,500,000, manufactured by G.A.F. Corporation) for 1 second and dried at 60° C. for 30 minutes. Then, it was further dipped in water for 3 hours for water contact and dried at 60° C. for 24 hours to obtain a surface lubricity imparted specimen (8).

The surface lubricity was good as in the preceeding Example.

EXAMPLE 7

A 3 cm×5 cm×0.4 mm (thick) piece of flexible polyvinyl chloride was dipped in a 1% MEK solution of 4,4'-diphenylmethane diisocyanate for 1 minute and dried at 60 ° C. for 30 minutes. It was then dipped in a solution of an ethyl ester (esterification degree: 40 to 50%) of a methyl vinyl ether-maleic anhydride copolymer (GANTREZ AN-170, MW=800,000, manufactured by G.A.F. Corporation) for 10 seconds and dried at 60° C. for 2 hours to obtain a surface lubricity treated specimen (21).

Specimen (21) was subjected to the frictional resistance and retention tests as will be described later. It was found that the frictional resistance $\mu$ of 0.02 was kept after a continuous water washing for 6 hours. However, the surface could not exhibit a low frictional resistance immediately after it had been wetted with water. The desired condition was reached after the lapse of some time.

Specimen (21) after its preparation was dipped in water at room temperature for about 30 minutes and dried at 60° C. for 24 hours to obtain a specimen (22).

Specimen (22) was subjected to the same tests as done on specimen (21). It was found that the frictional resistance $\mu$ of 0.02 was kept after a continuous water washing for 6 hours. Specimen (21) developed surface lubricity relatively rapidly after being wetted with water as opposed to specimen (21).

In addition, specimen (21) after its preparation was dipped in water at room temperature for more than one hour and dried at 60° C. for 24 hours to obtain a specimen (23).

Specimen (23) was subjected to the same tests as done on specimens (21) and (22). It was found that the frictional resistance $\mu$ of 0.02 was kept after a continuous water washing for 6 hours. Specimen (23) developed surface lubricity immediately after it had been wetted with water as compared with specimens (21) and (22).

EXAMPLE 8

A 3 cm×5 cm×0.4 mm (thick) piece of flexible polyvinyl chloride was dipped in an aqueous solution of 5 wt % diethylene triamine and 5 wt % tetra-n-butyl ammonium iodide at 60° C. for 10 minutes and dried at 60° C. for 30 minutes. It was then dipped in a 4% THF solution of a methyl vinyl ether-maleic anhydride copolymer ethyl ester for 10 seconds and dried at 60° C. for 24 hours. It was further dipped in water for about 1 hour for water treatment and dried at 60° C. for 24 hours to obtain a surface lubricity treated specimen (24).

Similar frictional resistance and retention tests were conducted on specimen (24) and the results were good.

EXAMPLE 9

A polyurethane resin terminated with an isocyanate group was synthesized by reacting 10 g of polyethylene glycol (MW=1,000), 4 g of pentaerythritol, and 16 g of toluene diisocyanate.

The polyurethane resin was molded into a sheet of 3 cm×5 cm×0.4 mm (thick). The sheet was dipped in a 4% THF solution of a half ethyl ester (esterification degree: 40 to 50%) of a methyl vinyl ether-maleic anhydride copolymer for 10 seconds and dried at 60° C. for 24 hours. It was then dipped in water at room temperature for more than 1 hour and dried at 60° C. for 24 hours to obtain a surface lubricity treated specimen (25).

In the frictional resistance and retention tests, specimen (25) showed as good results as in specimen (23).

EXAMPLE 10

A 3 cm×5 cm×0.4 mm (thick) sheet of 6-nylon was dipped in dilute hydrochloric acid at 30° C. for 60 minutes and sufficiently rinsed with water. It was then dipped in a 1:2 mixture of a 10% aqueous solution of polyethylene imine and a 5% methanol solution of dicyclohexyl carbodiimide at 30° C. for 5 hours, rinsed with water, dipped in a 4% THF solution of a half ethyl ester (esterification degree: 40 to 50%) of a methyl vinyl ether-maleic anhydride copolymer for 10 minutes, and dried at 60° C. for 2 hours. It was further dipped in water at room temperature for more than 1 hour for water contact and dried at 60° C. for 24 hours to obtain a surface lubricity treated specimen (26). This specimen showed excellent lubricity and retention in the frictional resistance and retention tests.

EXAMPLE 11

A stainless steel wire having a diameter of 0.87 mm and a length of 100 cm was dipped in a 1:1 mixture of a 5% THF solution of polyurethane and a 2% MEK solution of 4,4'-diphenylmethane diisocyanate and dried at 60° C. for 1 hour. It was then dipped in a 4% THF solution of an ethyl ester (esterification degree: 40 to 50%) of a methyl vinyl ether-maleic anhydride copolymer for 1 minute, dried at 60° C. for 30 minutes, dipped in water for about 3 hours for water contact and again dried at 60° C. for 24 hours to obtain a surface lubricity imparted catheter guide wire (27).

Guide wire (27) was wetted with physiological saline before it was inserted and operated through a 7Fr vasographic catheter. The performance was satisfactory with a very low sliding resistance.

EXAMPLE 12

A 3 cm×5 cm×0.4 mm (thick) sheet of 6-nylon was dipped in 1% MEK solution of 4,4'-diphenylmethane diisocyanate for 1 hour and dried at 60° C. for 30 minutes. It was then dipped in a 1% THF solution of a half ethyl ester (esterification degree: 40 to 50%) of a methyl vinyl ether-maleic anhydride copolymer for 1 second, dried at 60° C. for 30 minutes, dipped in water for about 3 hours for water treatment and dried at 60° C. for 24 hours to obtain a surface lubricity imparted specimen (28).

The surface lubricity was as good as in the foregoing Example.

No significant difference was found in the tests of frictional resistance and continuous water washing between Examples 1 to 6 or specimens (1) to (8) and Examples 7 to 12 or specimens (21) to (28). In a more severe test wherein the specimens were strongly squeezed with fingers in running water, Examples 7 to 12 were somewhat superior in the retention of surface lubricity.

EXAMPLE 13

A 3 cm×5 cm×0.4 mm (thick) sheet of polyurethane was dipped in a 0.6% MEK solution of 4,4'-diphenylmethane diisocyanate for 1 minute and dried at 60° C. for 30 minutes. It was then dipped in a 10% chloroform solution of a water-soluble nylon (Toray AQ Nylon P-70, trade name, manufactured by Toray Industries) for 1 second and dried at 60° C. for 6 hours. It was further contacted with water to obtain a surface lubricity treated specimen (31).

Test results were good with respect to both wet lubricity and retention.

EXAMPLE 14

A polyurethane sheet similar to that used in Example 13 was dipped in a 0.01% MEK solution of 4,4'-diphenylmethane diisocyanate for 1 minutes and dried at 60° C. for 30 minutes. It was then dipped in a 0.75% chloroform solution of hydroxypropyl cellulose (H type HPC, trade name, manufactured by Hercules Company) for 1 second and dried at 60° C. for 6 hours. After water treatment, a surface lubricity treated specimen (32) was obtained.

Test results were good with respect to both wet lubricity and retention.

EXAMPLE 15

PDAEM (poly-N,N-dimethylaminoethyl methacrylate) was synthesized by mixing 40 ml of DAEM (N,N-dimethylaminoethyl methacrylate), 10 ml of cyclohexane, and 0.5 g of AIBN, exposing the mixture to ultraviolet radiation for 2 hours, and drying the product in vacuum at 50° C. for 24 hours.

A mixture of 2 g of PDAEM, 1.4 ml of ethyl bromide and 18.2 ml of THF was thoroughly agitated and allowed to stand in an oven at 55° C. for 2 hours. Quaternized PDAEM formed a white precipitate which was dried in vacuum at 50° C. for 12 hours.

One part by volume of a 8% DMF solution of the quaternized PDAEM was mixed with one part by volume of a solution of PVC in THF and DMF (1:1) to prepare a quaternized PDAEM-doped PVC solution.

A stainless steel wire having a diameter of 0.87 mm and a length of 100 cm was immersed in the doped PVC solution for 1 minute and the thus coated wire dried in an oven at 60° C. for 2 hours.

The coated wire was immersed in a 0.25% aqueous solution of an anionic polyacrylamide (MA-3000-6H) for 1 hour and dried at 60° C. for 2 hours, obtaining a surface lubricity-imparted catheter guide wire (15).

Guide wire (15) was wetted with physiological saline before it was inserted and operated through a 7Fr vasographic catheter. The performance was satisfactory with a very low sliding resistance.

EXAMPLE 16

A nylon sheet similar to that used in Example 4 was coated with the isocyanate-terminated polyurethane resin synthesized in Example 3. The coated sheet was then immersed in a 5% chloroform solution of polyvinyl pyrrolidone (K-90, average molecular weight 360,000, manufactured by GAF Corporation) and dried, obtaining a specimen (16) having the coating layer attached to the substrate material through ionic bond. Specimens (1) to (6) of the present invention and specimen (15) of this example all exhibited improved surface lubricity in the frictional resistance test and retention test-I, although a little difference was observed in the latter test. In the retention test-II, however, specimen (16) apparently lost lubricity whereas specimens (1) to (6) of the present invention well retained their initial lubricity. Catheters were prepared by the same procedures as for specimens (1) to (6) and specimen (16). The catheter corresponding to specimen (16) experienced the separation of the urethane layer near catheter side holes and along a boundary with an untreated section. The effectiveness of the present invention was thus proved.

COMPARATIVE EXAMPLE 1

Several specimens were prepared to dimensions of 3 cm×5 cm×0.4 mm (thick). Specimen (9) was a flexible polyvinyl chloride sheet coated with glycerine, specimen (10) was a similar sheet coated with olive oil, and specimen (11) was a similar sheet having no coat thereon. Specimens (12), (13), and (14) were formed from low density polyethylene, high density polyethylene, and tetrafluoroethylene, respectively. These specimens were subjected to the same frictional resistance test and retention test-I were conducted and compared with specimens (1) to (8). The specimens other than those of the present invention originally had high frictional resistance or lost their initial lubricity after a continuous water washing for about 10 minutes. The effectiveness of the present invention was proved.

Frictional Resistance Test

Figure 5:
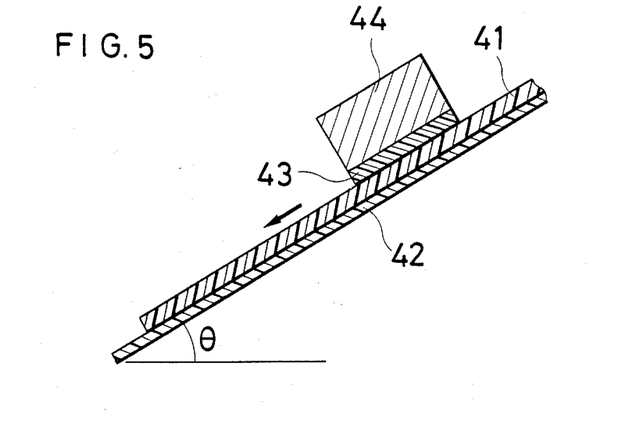
FIG. 5 illustrates a method of measuring frictional resistance.

A polyvinyl chloride or polyurethane sheet 41 which was so treated as to have a coating of the present invention or of a comparative example was fixed on a ramp 42. A cylindrical iron weight 44 of about 100 g having a polyamide resin sheet 43 attached to the bottom thereof was placed on the sheet 41 as shown in FIG. 5.

The inclination angle θ of the ramp 42 was gradually increased to determine the angle θ when the weight began to move. The coefficient of friction was obtained from μ=tan θ. The results are shown in Table 1.

Glycerine coat specimen (9) and olive oil coat specimen (10) were prepared by dipping a polyvinyl chloride sheet in the corresponding coating liquid and draining the sheet of the liquid so that the liquid might not drip.

Retention Test-I (change of frictional resistance with time)

Figure 6:
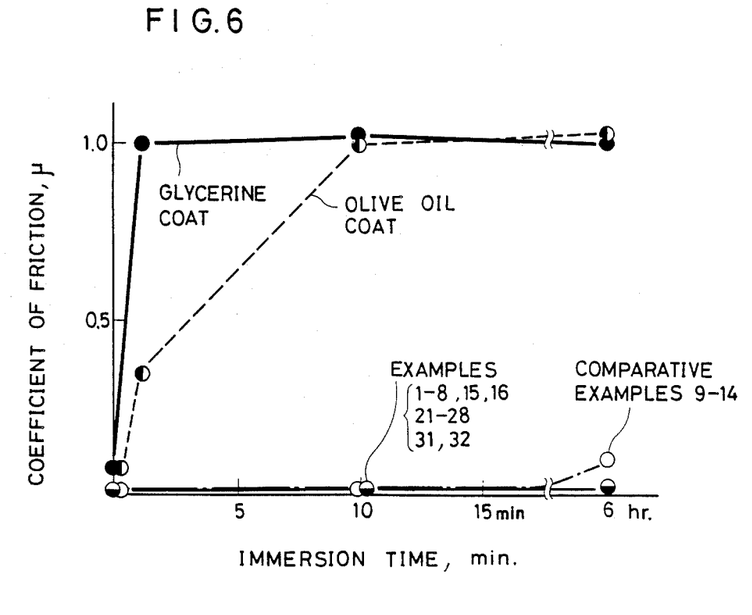
FIG. 6 is a graph showing a change of the coefficient of friction of various specimens with time.

The specimens having the coating layers as specified in Examples of the present invention and having olive oil and glycerine coats were dipped in one liter of water which was stirred at 500 to 600 rpm. The thus treated specimens were measured for coefficient of friction by the method shown in FIG. 5. The changes of coefficient of friction with time were examined. The results are shown in Table 1 and FIG. 6.

Retention Test-II (change of lubricity after severe friction)

The specimens of Examples and Comparative Examples were strongly rubbed on the surface with a wet finger to examine whether or not the original lubricity was retained. The results are shown in Table 1.

TABLE 1

| Specimen No. | Frictional Resistance | Surface lubricity Retention-I | Retention-II | Remarks |
|---|---|---|---|---|
| 1 | 0.02 | E | E | G | |
| 2 | 0.02 | E | E | G | |
| 3 | 0.02 | E | E | G | |
| 4 | 0.02 | E | E | G | |
| 5 | 0.02 | E | E | G | |
| 6 | 0.02 | E | E | G | |
| 7 | — | E | E | G | |
| 8 | 0.02 | E | E | G | |
| 9* | 0.08 | G | P | P | Glycerine coat |
| 10* | 0.08 | G | P | P | Olive oil coat |
| 11* | 1.04 | P | — | — | No coat |
| 12* | 0.69 | F | — | — | Low density polyethylene |
| 13* | 0.40 | F | — | — | High density polyethylene |
| 14* | 0.36 | F | — | — | Tetrafluoroethylene |
| 15 | — | E | E | P | |
| 16 | 0.02 | E | E | P | |
| 21 | 0.02 | E | E | E | |
| 22 | 0.02 | E | E | E | |
| 23 | 0.02 | E | E | E | |
| 24 | 0.02 | E | E | E | |
| 25 | 0.02 | E | E | E | |
| 26 | 0.02 | E | E | E | |
| 27 | — | E | E | E | |
| 28 | 0.02 | E | E | E | |
| 31 | 0.02 | E | E | G | |
| 32 | 0.02 | E | E | G | |

*Comparative Examples
**E = excellent, G = good, F = fair, P = poor

What is claimed is:

1. A medical instrument comprising:
a substrate inherently having a reactive functional group on a surface thereof;
a water soluble polymer selected from the class consisting of a cellulosic polymer, a maleic anhydride polymer, and a water soluble nylon, or a derivative thereof, said water soluble polymer being covalently bonded with said reactive functional group, said surface exhibiting lubricity when wetted with aqueous fluid.

2. A medical instrument as claimed in claim 1 wherein said cellulosic polymer is hydroxypropyl cellulose.

3. A medical instrument as claimed in claim 1 wherein said maleic anhydride polymer is a copolymer of methyl vinyl ether and maleic anhydride.

4. A medical instrument as claimed in claim 1 wherein said reactive functional group is selected from the class consisting of aldehyde, epoxy, isocyanate, and amino groups.

5. A medical instrument as claimed in claim 1 wherein said medical instrument is a guide member formed of a wire member insertable through a medical tubing for enabling said medical tubing to be moved into and out of a body.

6. A medical instrument as claimed in claim 1, wherein said water-soluble polymer has an average molecular weight of 30,000 to 5,000,000.

7. A method for preparing a medical instrument comprising:
treating a substrate constituting said medical instrument, said substrate having a surface, with a solution of a compound having a reactive functional group to form an undercoat so that said reactive functional group is present at least on said surface of said substrate; and
treating said substrate with a water-soluble polymer selected from the class consisting of a cellulosic polymer, a maleic anhydride polymer, and a water-soluble nylon, or a derivative thereof, to covalently bond said reactive functional group with said water-soluble polymer to form a coat of said water-soluble polymer on said undercoat so that said surface has lubricity when wetted.

8. A method for preparing a medical instrument as claimed in claim 7 wherein said cellulosic polymer is hydroxypropyl cellulose.

9. A method for, preparing a medical instrument as claimed in claim 7 wherein said maleic anhydride polymer is a copolymer of methyl vinyl ether and maleic anhydride.

10. A method for preparing a medical instrument as claimed in claim 7 wherein said reactive functional group is selected from the class consisting of aldehyde, epoxy, isocyanate, and amino groups.

11. A method for preparing a medical instrument as claimed in claim 7 wherein said medical instrument is a guide member formed of a wire member insertable through a medical tubing for enabling said medical tubing to be moved into and out of a body.

12. A method for preparing a medical instrument as claimed in claim 7, which further comprises contacting the treated substrate with water.

13. A method for preparing a medical instrument as claimed in claim 7 wherein said water-soluble polymer has an average molecular weight of 30,000 to 5,000,000.

14. A medical instrument comprising:
   a substantially reactive functional group-free substrate having a surface;
   an undercoat formed on said surface from a compound having a reactive functional group;
   a coating of a water-soluble polymer selected from the class consisting of a cellulosic polymer, a maleic anhydride polymer, and a water soluble nylon, or a derivative thereof, said water-soluble polymer being covalently bonded with said reactive functional group, said surface exhibiting lubricity when wetted with aqueous fluid.

15. A medical instrument as claimed in claim 14 wherein said cellulosic polymer is hydroxypropyl cellulose.

16. A medical instrument as claimed in claim 14 wherein said maleic anhydride polymer is a copolymer of methyl vinyl ether and maleic anhydride.

17. A medical instrument as claimed in claim 14 wherein said reactive functional group is selected from the class consisting of aldehyde, epoxy, isocyanate, and amino groups.

18. A medical instrument as claimed in claim 14 wherein said medical instrument is a guide member formed of a wire member insertable through a medical tubing for enabling said medical tubing to be moved into and out of a body.

19. A medical instrument as claimed in claim 14 wherein said water-soluble polymer has an average molecular weight of 30,000 to 5,000,000.

20. A medical instrument as claimed in claim 14 wherein said medical instrument is a guided member formed of a wire member insertable through a medical tubing for enabling said medical tubing to be moved into and out of a body.

21. A method for preparing a medical instrument as claimed in claim 14, which further comprises contacting the treated substrate with water.

22. A method for preparing a medical instrument comprising:
   forming a surface of said medical instrument with a substrate inherently having a reactive functional group on a surface thereof; and
   treating said substrate with a water-soluble polymer selected from the class consisting of a cellulosic polymer, a maleic anhydride polymer, and a water-soluble nylon, or a derivative thereof, to covalently bond said reactive functional group with said water-soluble polymer to form a coat of said water-soluble polymer on said surface so that said surface exhibits lubricity when wetted.

23. A method for preparing a medical instrument as claimed in claim 22 wherein said cellulosic polymer is hydroxypropyl cellulose.

24. A method for preparing a medical instrument as claimed in claim 22 wherein said maleic anhydride polymer is a copolymer of methyl vinyl ether and maleic anhydride.

25. A method for preparing a medical instrument as claimed in claim 22 wherein said reactive functional group is selected from the class consisting of aldehyde epoxy, isocyanate, and amino groups.

26. A method for preparing a medical instrument as claimed in claim 22 wherein said water-soluble polymer has a average molecular weight of 30,000 to 5,000,000.

* * * * *

UNITED STATES PATENT AND TRADEMARK OFFICE
CERTIFICATE OF CORRECTION

PATENT NO. : 4,876,126

DATED : October 24, 1989

INVENTOR(S) : TAKEMURA et al

It is certified that error appears in the above-identified patent and that said Letters Patent is hereby corrected as shown below:

COLUMN 3, LINE 34:

Reads: "ha"
    Should Read: --has--.

COLUMN 7, LINE 23:

Reads: "tereohthalaldehyde,"
    Should Read: --terephthalaldehyde,--.

COLUMN 12, LINE 10:

Reads: "u"
    Should Read: --$\mu$--.

COLUMN 14, LINE 59:

Reads: "(26). This"
    Should Read: --(26).
                    This-- (begin new paragraph with This).

UNITED STATES PATENT AND TRADEMARK OFFICE
CERTIFICATE OF CORRECTION

PATENT NO. : 4,876,126

DATED : October 24, 1989

INVENTOR(S) : TAKEMURA et al

It is certified that error appears in the above-identified patent and that said Letters Patent is hereby corrected as shown below:

COLUMN 18, LINE 63:

Reads: "for, preparing"
    Should Read: --for preparing--.

Signed and Sealed this

Twenty-second Day of January, 1991

Attest:

HARRY F. MANBECK, JR.

*Attesting Officer*    *Commissioner of Patents and Trademarks*